United States Patent [19]

McLaughlin

[11] Patent Number: 4,579,530

[45] Date of Patent: Apr. 1, 1986

[54] FABRICATION OF PORCELAIN RESTORATIONS

[76] Inventor: Gerald G. McLaughlin, 550 Rte. 25A, Rocky Point, N.Y. 11778

[21] Appl. No.: 673,711

[22] Filed: Nov. 21, 1984

[51] Int. Cl.⁴ .............................................. A61C 5/10
[52] U.S. Cl. .................................... 433/223; 433/213; 264/19
[58] Field of Search ............... 433/223, 213, 202, 203, 433/212, 215, 218, 222; 264/19, 20

[56] References Cited

U.S. PATENT DOCUMENTS

| Re. 22,331 | 6/1943 | Myerson | 433/203 |
|---|---|---|---|
| 3,464,837 | 9/1969 | McLean et al. | 433/202 |
| 3,541,688 | 11/1970 | McLean et al. | 433/222 |
| 3,834,024 | 9/1974 | Kochavi | 433/218 |
| 3,934,348 | 1/1976 | Janjie | 433/223 |
| 3,986,261 | 10/1976 | Faunce | 433/217 |
| 4,307,044 | 12/1981 | Perez | 264/19 |
| 4,433,959 | 2/1984 | Faunce | 106/35 |
| 4,473,353 | 9/1984 | Greggs | 433/215 |

FOREIGN PATENT DOCUMENTS 51235 2/1936 Denmark ........................ 433/218

Primary Examiner—John J. Wilson
Attorney, Agent, or Firm—Leonard Belkin

[57] ABSTRACT

A method of fabricating a porcelain veneer casing for use in the restoration of damaged teeth in which a porcelain layer is built up on a model of the teeth. The model is removed by erosion caused by the blast of air under pressure containing glass balls. The invention also includes the method of restoration of damaged teeth using the aforesaid porcelain veneer casing and the porcelain veneer casing as an article of manufacture.

7 Claims, 4 Drawing Figures

FABRICATION OF PORCELAIN RESTORATIONS

BACKGROUND OF THE INVENTION

This invention relates generally to veneer restoration of teeth and more particularly to an improved porcelain veneer and method of forming and applying to teeth a glazed porcelain labial veneer or restoration.

As noted in the extensive discussions of the restoration of teeth by the applications of laminar overlays in U.S. Pat. Nos. 3,986,261 and 4,433,959 issued to Faunce and 4,473,353 issued to Greggs, many structural and cosmetic deficiencies of teeth can be corrected by the preparation and bonding permanently to the tooth being treated an outer layer thereby creating a new veneer. For many types of situations, such a procedure is a marked improvement over the formation of a crown which involves the use of expensive metal materials, such as gold, and extensive dental chair time to reduce drastically or reshape the affected tooth.

In the earlier Faunce patent noted above method and apparatus are taught to restore teeth by adhering to the teeth a properly colored polymerized, preformed plastic facing. In the later Faunce patent, the concept is improved upon by presenting the use of a composite laminate dental veneer in which it is possible to combine an inner lamination capable of efficient bonding to the labial enamel surface of the tooth with an outer lamination composed of dense, stain-resistant materials such as a cross-linked polymer and various vitreous materials such as ceramic material, glass and the like. An additive and subtractive color system is employed in the outer laminate to achieve the desired cosmetic effect.

The use of plastic and plastic-based materials to accomplish the tooth restoration while in many ways and situations an improvement over the use of crowns does suffer certain drawbacks which limit their usefulness and application. Due to the porosity of plastic materials, there are problems of long-term color stability, while wear resistance tends to be low. When laminates are employed, the thickness required for their most effective use has been found in many cases to lead to inflammation of gingival tissue. Other problems which have appeared relate to toxicity of materials themselves and difficulties involved in obtaining the desired color.

The patent to Greggs teaches the cosmetic restoration of teeth employing for the labial veneer a glazed porcelain material custom made for a patient's tooth and thereafter chemically and mechanically bonded to the tooth. The use of porcelain avoids many of the drawbacks and problems associated with plastic materials, however, in the method taught by Greggs there are certain limitations and deficiencies. The method taught by the patentee is to prepare initially a model of the patient's tooth or teeth from which is prepared a Pindex model. After trimming and undercutting the tooth die, platinum foil is placed over the labial surface of the tooth die. The platinum matrix is removed for decontamination and then replaced on the die for brushing with porcelain powder. The foil matrix is removed for firing and then replaced on the die for finishing, trimming, and contouring. The matrix is again removed from the die for cleaning and separation of the foil from the porcelain veneer. The tooth and veneer are treated at their contacting surfaces and the venner then bonded to the tooth.

In the patented method of Greggs briefly described above, some of the tooth, especially at the bottom, must be stripped away to accommodate the thickness of the platinum foil. In addition, the frequent mounting and removal of the porcelain requires the veneer to be thicker along the edges than is actually required on the tooth. Furthermore, when the metal foil is peeled away from the veneer, some of the porcelain along its edges is removed as well creating problems of providing a smooth transition from the procelain veneer to the tooth. The peeling away process just described, which is done in the laboratory, has proven to be a little tricky since the platinum has to be teased away from the porcelain, incurring a risk that the veneer will be damaged and the whole process has to be repeated.

SUMMARY OF THE INVENTION

The present invention overcomes or reduces the problems and drawbacks associated with current techniques of veneer restoration of teeth employing porcelain.

This is accomplished in the present invention by preparing the veneer without using a metal matrix as an intermediary.

A preferred embodiment of this invention is a method of fabricating a porcelain labial veneer or restoration for a tooth which comprises first forming an impression of the tooth utilizing conventional material followed by preparing from said impression a statue of the tooth out of a suitable refractory investment type material.

Porcelain powder formed in a liquid slurry is then brushed on the labial surface of the statue to build up a veneer casing conforming to the shape of the bonding surface of the tooth followed by firing the veneer casing of the statue.

In order to exercise greater control over the pigmentation and appearance of the veneer, the veneer casing can be prepared by producing two bakes. In accordance with this method, the first layer of porcelain powder brushed on the labial surface of the statue is made substantially thinner than when only a single bake is employed. When the first layer is baked, producing the veneer casing mounted on the statue, after cooling additional porcelain powder in a liquid slurry is brushed on to fill in all cracks which are present due to the thinness of the first layer and cover the edge of the first bake. The second layer is applied to bring up the thickness to the desired value. The casing on the statue is then fired again to produce the second bake.

After cooling, the statue is then removed from the porcelain veneer by blasting with an abrasive material whose hardness is sufficient to erode away the investment material but not hard enough to damage the porcelain.

The veneer casing produced by either the single or double bake process is then touched up to smooth all edges and remove all visible undercuts and, if desired, a glazing may be added. After cleaning, the interior surface of the veneer casing and the engaging surfaces of the tooth are etched and coated with a suitable cement to permit the veneer to be mounted and fixed in place.

The resulting veneer mounted on the tooth when made in accordance with the principles of this invention is thinner along the edge than porcelain veneers made by techniques employed up to now so that less trimming of the tooth, hence less dental chair time, is required. Furthermore, the method conducted in accordance with this invention exposes the veneer during its fabrication to less risk to being damaged since less in the way of laboratory skill is required, and a smoother transition of veneer to teeth is possible since the exposed edge is thin, and remains smooth and undamaged during production.

Utilizing the principles of this invention, other types of restorations are possible, such as inlays, onlays, or a combination of both.

It is thus a principal object of this invention to provide a method of fabricating a porcelain labial veneer for the restoration of teeth having improved qualities of finish and construction.

It is another object of this invention to provide a method of fabricating a porcelain labial veneer for the restoration of teeth in which there is reduced risk of damage to the veneer during manufacture.

It is still another object of this invention to provide a method of porcelain veneer restoration of teeth in which the veneer is thinner along the edge than heretofore has been possible with the result that less alteration of the teeth is required in preparation for mounting of the veneer.

Other objects and advantages of this invention will hereinafter become obvious from the following description of preferred embodiments of this invention.

DETAILED DESCRIPTION OF THE PREFERRED EMBODIMENTS

Figure 1:
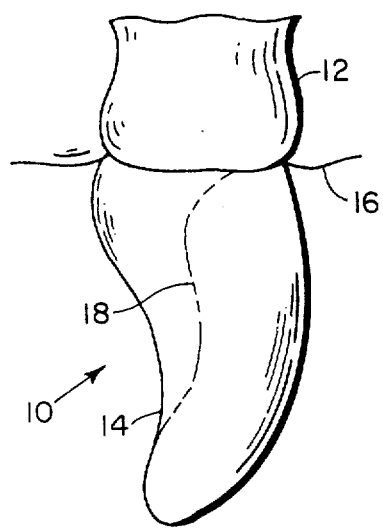
FIG. 1 is a side elevational view of the anterior tooth showing a porcelain labial veneer bonded thereon.
Figure 2:
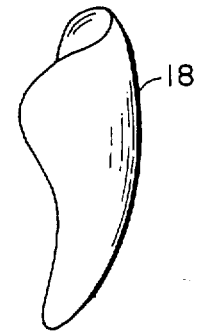
FIG. 2 is an isometric view of a veneer casing prepared in accordance with this invention.

Referring to FIGS. 1 and 2, there is shown an anterior incisor tooth 10 consisting of a root portion 12 and a crown portion 14 positioned relative to the gingival margin 16.

In accordance with the principles of this invention, tooth 10 is provided with a porcelain labial veneer 18 whose outline on crown portion 14 is illustrated in phantom because the edge of veneer 18 would not ordinarily be visible since the edge is blended into the tooth.

In order to fabricate porcelain veneer 18, a mold is formed from the tooth, or teeth which are adjacent to each other, utilizing any suitable technique or material now available to dentists for producing a mold having the right elasticity after hardening to permit convenient removal without alteration of the casting.

A model or statue of the tooth or teeth is then produced from the mold utilizing a suitable refractory investment or casting material. The investment material is not critical except that it should be capable of withstanding the high temperatures necessary to fire the porcelain and not be as hard as the porcelain veneer to be fabricated, for reasons which will later become obvious. A refractory porcelain investment material manufactured by Whip Mix Corp. and marketed by Chameleon Dental Products under their own label has been found to be suitable as well as other compositions being marketed by other companies. After being formed, the statue is cured and removed from the mold.

As the preparation of the veneer casing using two layers of porcelain and two separate bakes produces a veneer which is more esthetically appealing than one produced from a single layer due to better control over pigmentation, this method will be described first.

An opaque water slurry is prepared from porcelain powder. Dental quality porcelain powder is available commercially, for example, Microbond brand of porcelain powder manufactured by Austenal Corp. The addition of a pigment renders the porcelain opaque.

The slurry is brushed on the labial surface of the statue until a uniform thickness in the general contour is in the range of about 0.3 to 0.5 mm. The thickness is shaped down to a thin edge along the perimeter of the veneer casing.

Figure 3:
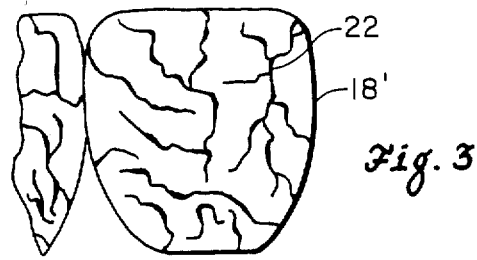
FIG. 3 is a detail of the surfaces of adjacent porcelain veneer casings after the first bake where more than one bake is employed.

The statue with the coating of the slurry brushed on is placed in a properly preheated oven until the porcelain veneer is cured, producing the first bake. The statue is then removed and cooled. The porcelain veneer casing has the appearance of a dried out river bed with a very cracked surface as shown in FIG. 3. Single layer veneer casing 18' is glazed in appearance with cracks 22 distributed throughout in the manner illustrated.

A second layer of porcelain slurry is then brushed over the cured first bake except that, for cosmetic purposes, an opaque slurry is brushed on the main body while the incisal portion of the veneer is brushed with transparent (unpigmented) slurry. The total thickness is built up to about 1 mm total maximum thickness of the veneer. (After firing, it has been found that the veneer at its thickest point will be in the range of 0.5 to 0.7 mm thick.) When the second layer is brushed on, slurry thickness should be shaped down to a narrow edge along the perimeter of the veneer with some of the slurry overlapping slightly the edge of the first bake to insure that there will be no lifting of porcelain during the second bake.

The statue with the veneer casing still mounted is then fired once again to cure the porcelain. After cooling, the veneer casing will have a flaw-free appearance. While still on the statue, the veneer casing may be subject to a finishing treatment to improve the esthetics, such as bevel the incisal edge and feather the embrasures and the marginal areas as close as possible to the finished margin. Also a glaze may be added. The support provided by the statue with the casing still mounted while such treatment is conducted is a feature of this invention.

Once the veneer casing is finished to the satisfaction of the professional, the next step is to remove the veneer casing from the statue without damaging or risking damage to the casing. This is accomplished by blasting away the deposit material making up the statue with an abrasive material which is harder than the investment material but not hard enough to damage the porcelain. It has been found that blasting the statue with air under pressure carrying an abrasive powder such as glass beads of small diameter in the order of 50 microns will erode away the deposit material and leave the inside of the casing undamaged.

Figure 4:
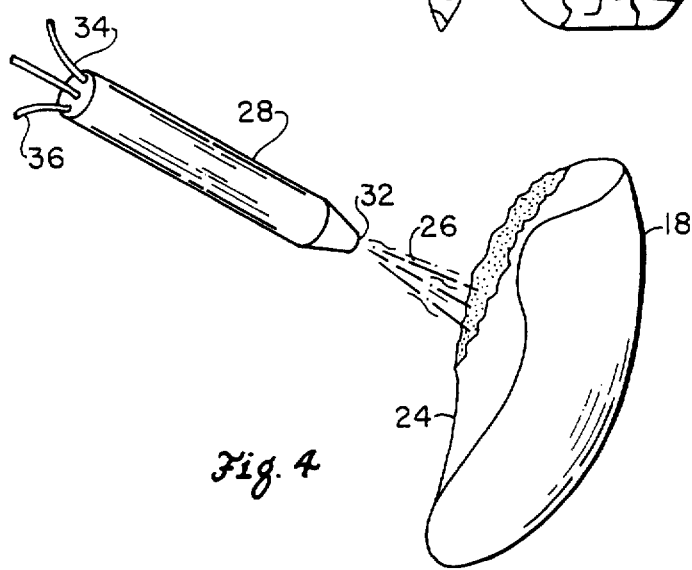
FIG. 4 shows an arrangement for eroding the investment material from the inside of a casing.

As seen in FIG. 4, statue 24 having mounted thereon finished veneer casing 18 is blasted by a jet 26 of air containing fine glass beads. Tool 28 employing a nozzle 32 is supplied with air under pressure from hose 34 with a hose 36 to pick up the glass beads which are so small that they have the appearance of a fine sand drawn from a separate cannister, not shown. Such blasting equipment is conventional. Tool 28 and statue 24 with veneer casing 18 thereon are hand held.

Casing 18 is then cleaned and sterilized, and the tooth is usually prepared by cleaning and etching the surface to be mated with a suitable acid such as hydrofluoric on the casing and phosphoric on the tooth. A suitable cement or adhesive is then applied to the surfaces to be joined and the veneer casing is slipped over the tooth. If the casing encompasses more than one tooth, it may be desirable to separate the veneer casings before mounting the casings on the teeth.

When it is desired to produce veneer casing 18 out of a single layer, the powdered porcelain is brushed on the statue to a thickness of about 1 mm trimmed down to a narrow edge. In this situation, the degree of pigmentation, that is, opaqueness, of the slurry would vary over the casing. Once fired, the casing would be treated and removed from the statue in the same manner as is the second bake in the preceding process.

EXAMPLE

Porcelain veneers have been fabricated and mounted successfully in accordance with the principles of this invention as described above. The following is one example of the two bake method.

1. Chameleon duplicating material incorporating the specified catalyst was packed around the teeth surfaces to be duplicated. After the material remained in impression until the tackiness was gone (about ten minutes) the mold was removed.
2. The inside surface of the mold was coated with a thin layer of Chameleon debubblizer.
3. The Chameleon investment material was prepared in accordance with the instructions of the manufacturer. Using a spatula, investment material was transferred to the mold until all teeth were filled, while the mold was being vibrated.
4. After the investment material hardened for at least an hour but not more than two hours, mold was removed and the casting or statue was fired under vacuum at the temperature specified by the manufacturer of the material, to eliminate gas and harden the surface. Excessive bulk material was removed from the statue.
5. An opaque porcelain slurry was prepared from Chameleon powdered porcelain, pigmentation, and water according to instructions of the manufacturer. The porcelain slurry was brushed on the statue teasing the porcelain to the edge of the model. This process was continued until porcelain was built up to 0.3 to 0.55 mm thickness. Tapping of the statue condensed out the porcelain and the water was blotted up.
6. The statue with the layer of porcelain thereon was then fired under conditions specified by the manufacturer of the porcelain followed by bench cooling, completing the first bake.
7. Transparent porcelain slurry was brushed on the incised area while opaque slurry was brushed on the remaining reas until a thickness no greater than 1 mm was reached. All cracks were filled in. The porcelain was contoured down to a very thin layer at the edge and overlapped slightly the cured edge.
8. The statue with the casing mounted was fired once again and bench cooled to complete the second bake. After the second firing, the veneer casing had a flawfree appearance.
9. The casing was then cut into individual teeth pieces and embrasures filled in with porcelain slurry and the surfaces covered with a glaze extending 1 mm beyond the edges to improve the appearance of the veneer. The casings were then fired.
10. The investment material was removed from the veneer casings by blasting the material with air under pressure containing glass beads, eroding away the material, leaving the casings ready to be fitted to and cemented on the teeth for which they were custom fitted.

In the description of the preferred embodiments of this invention reference has been made to labial veneer casing or casings. It is understood, however, that the invention is equally applicable to the production of, and includes, a restoration or restorations and the word restoration herein is meant to include a layer or layers mounted or for being mounted on a tooth or teeth to act as a veneer, inlay, onlay, or any combination of the foregoing.

In the methods described above, the veener casing is custom-made for a particular patient. It should be understood, however, that a series of casings can be prepared in advance for a variety of sizes and shapes of teeth so that a dentist can select one which roughly fits a tooth to be restored, and cement or adhesive can then be employed to fill up any spaces between the casing and the tooth. In this way, the benefits of this type of restoration can be enjoyed at less than the costs of custom making each veneer one at a time to order.

While only certain preferred embodiments of this invention have been described it is understood that a variety of modifications and changes are possible without departing from the principles of this invention. Thus the invention is to be defined and limited not by the examples described above but only by the claims which follow.

What is claimed is:

1. A method of fabricating a custom-made procelain restoration for a tooth without the use of a metal matrix comprising the steps of:
   a. preparing an impression of said tooth;
   b. forming from said impression a statue of said tooth out of an investment material;
   c. applying porcelain powder to the surface of said statue to build a veneer restoration conforming to the shape of the bonding surface of said tooth;
   d. firing the porcelain restoration on said statue;
   e. eroding away said statue from said porcelain restoration leaving said restoration ready for mounting on said tooth.

2. The method of claim 1 in which the step of eroding away said statue from said porcelain restoration is accomplished by blasting the former with air under pressure containing particles sufficiently hard to remove the investment material but insufficiently hard to damage the formed porcelain restoration.

3. A method of fabricating a porcelain restoration for a tooth without the use of a metal matrix comprising the steps of:
   a. preparing an impression of said tooth;
   b. forming from said impression a statue of said tooth out of an investment material;
   c. applying porcelain powder to the surface of said statue to build a restoration conforming to the shape of the bonding surface of said tooth;
   d. firing the porcelain restoration on said statue to form a first bake;
   e. applying additional porcelain powder to said restoration in sufficient quantity and at specific areas to fill in all cracks and to add a second layer of porcelain;

f. firing the porcelain restoration on said statue to form a second bake; and g. eroding away said statue from said porcelain restoration leaving said restoration ready for mounting on said tooth.

4. The method of claim 3 in which said additional porcelain powder when applied is made to overlap the edge of said first bake.

5. A method for the restoration of a defective tooth comprising:
   a. preparing a porcelain restoration by forming a fired porcelain layer on a model of said tooth made from a refractory investment material;
   b. eroding away said investment material from said restoration;
   c. fitting on and adhering said restoration to said tooth to form a smooth and esthetically attractive restoration surface on said tooth.

6. The method of claim 5 in which said investment material is eroded away by sand blasting.

7. A method for the restoration of a defective tooth comprising:
   a. preparing without the use of a metal matrix a porcelain restoration by forming a first fired porcelain layer on an exact model of said tooth thereby conforming to the surface of said tooth followed by imposing thereon a second fired porcelain layer which overlaps the edge of said first layer;
   b. removing said model by blasting the latter with air under pressure containing particles of sufficient hardness to erode away the material of said model but of insufficient hardness to damage said restoration; and
   c. fitting on and adhering said restoration to said tooth to form a smooth and esthetically attractive restoration surface on said tooth.

* * * * *

REEXAMINATION CERTIFICATE (1099th)
United States Patent [19]

McLaughlin

[11] B1 4,579,530

[45] Certificate Issued   Jul. 11, 1989

[54] FABRICATION OF PORCELAIN RESTORATIONS

[75] Inventor: Gerald G. McLaughlin, Rocky Point, N.Y.

[73] Assignee: Yukiyo Limited

Reexamination Request:
No. 90/001,125, Nov. 13, 1986

Reexamination Certificate for:
Patent No.: 4,579,530
Issued: Apr. 1, 1986
Appl. No.: 673,711
Filed: Nov. 21, 1984

[51] Int. Cl.⁴ ............................................... A61C 5/10
[52] U.S. Cl. ..................................... 433/223; 433/213; 264/19
[58] Field of Search ............... 433/223, 213, 202, 203, 433/212, 215, 218, 222, 88; 264/19, 20

[56] References Cited

PUBLICATIONS

J. H. Mosteller et al., "Clinical and Laboratory Procedures for Class V Porcelain Inlays", *Journal of the Alabama Dental Association,* 49(4), pp. 27-37 (Aug. 1965).
R. L. Kinzer, "Porcelain Inlays Utilizing Retentive Pins", *Journal of the Indiana Dental Association,* 53, 8-10 (Mar.-Apr. 1974).
R. K. George, "Porcelain Inlays Baked in Investment Matrix", *Dental Digest,* 62, 549-551 (1956).
A. Dinnis, "Porcelain Work on Non-Metallic Bases", *Dental Cosmos,* 56, 997-98 (1914).
D. T. Barcroft, "Baking Porcelain Inlays Directly in the Investment Without the Use of a Platinum Matrix", *The Journal of the American Dental Association,* 28, 97-99 (1941).
R. L. Kinzer et al., "Preliminary Report: High Heat Investment in Constructing Porcelain Restorations", *Journal of the Southern California Dental Association,* 30, 314-317 (1962).
R. K. George, "Construction of Porcelain Inlays Without a Platinum Matrix", *Dental Digest,* 41, 80, 81, 93 (1935).
M. E. Warnick et al., "Indirect Technique for Making Porcelain Inlays", *Journal of Prosthetic Dentistry,* 11, 948-958 (1961).
A. F. Cameron, "Manufacture of Vacuum Fired Porcelain Inlays", *NACDL Journal,* 16, 7-8 (Apr. 1969).
A. J. Ehleider, "New Porcelain Inlay Technic Requires No Platinum Matrix", *Dental Survey* (Jun. 1944).
T. Kramer, "Technic for Producing Porcelain Facings With V.H.T. Industrial Investment", Whip Mix Corporation laboratory directions (Sep. 1984).
J. R. Calamia, "Etched Porcelain Facial Veneers: A New Treatment Modality Based on Scientific and Clinical Evidence", *Journal of Dental Research,* pp. 255-259 (Sep.-Oct. 1983).
Comco, Inc. brochure, "Micro Blaster" and attachments (Copyright 1974, Revision of Aug. 1976).
Penwalt Company advertising brochure, "JELENKO" JelBlast Sandblasting Unit (Mar. 29, 1976).
*Dental Abstracts,* Advertisement—"Abrasi-Jet" (Jun 1974).
N. Martinelli et al., *Dental Laboratory Technology,* Third Edition, The C. V. Mosby Company, p. 7 (1981).
J. M. Petrie, "The Construction of Porcelain Inlays Without the Use of Foil", *The Dental Gazette,* pp. 28, 444-446 (May 1940).
F. J. Ballard, "Construction of Porcelain Inlays Without the Use of Foil", *The Dental Gazette,* 6, 502 (1940).
H. A. Erickson, "The Porcelain Inlay Without the Use of the Platinum Matrix", *The Minneapolis District Dental Journal,* pp. 30-32 (Oct. 27, 1937).
D. T. Barcroft, "Baking Porcelain Inlays Directly on the Investment", *Dental Digest,* 41, 318-21 (1935).
E. K. Joseph, "A New Approach to Porcelain Inlays", *The Dental Practitioner,* vol. X, No. 12, pp. 263-266 (Aug. 1960).
J. P. Cooney, et al. "Type III Gold Alloy Complete Crowns Cast in a Phosphate-Bonded Investment", *Journal of Prosthetic Dentistry,* 46, 414-419 (Oct. 1981).

*Primary Examiner*—John J. Wilson

[57] ABSTRACT

A method of fabricating a porcelain veneer casing for use in the restoration of damaged teeth in which a porcelain layer is built up on a model of the teeth. The model is removed by erosion caused by the blast of air under pressure containing glass balls. The invention also includes the method of restoration of damaged teeth using the aforesaid porcelain veneer casing and the porcelain veneer casing as an article of manufacture.

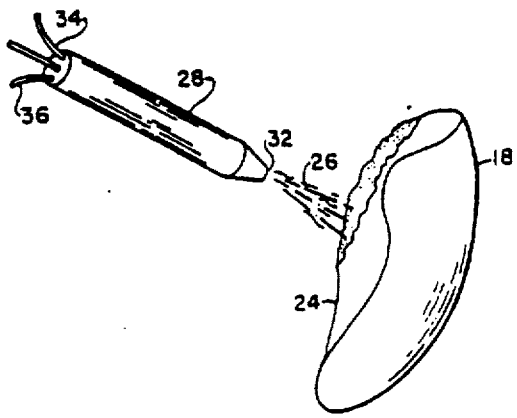

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3-7 are cancelled.

Claims 1 and 2 are determined to be patentable as amended.

New claims 8-11 are added and determined to be patentable.

1. A method of fabricating a custom-made porcelain veneer restoration for a tooth without the use of a metal matrix comprising the steps of:
   a. preparing an impression of said tooth;
   b. forming from said impression a statue of said tooth out of an investment material;
   c. applying porcelain powder to the surface of said statue to build [a] *said* veneer restoration conforming to the shape of the bonding surface of said tooth;
   d. firing the porcelain veneer restoration on said statue; *and*
   e. eroding away said statue from said porcelain veneer restoration leaving said restoration ready for mounting on said tooth.

2. The method of claim 1 in which the step of eroding away said statue from said porcelain veneer restoration is accomplished by blasting the former with air under pressure containing particles sufficiently hard to remove the investment material but insufficiently hard to damage the formed porcelain veneer restoration.

*8. The method of claim 2 in which said particles comprise an abrasive powder consisting of glass beads.*

*9. The method of claim 1 in which additional porcelain powder is applied to said veneer restoration prior to eroding away said statue in sufficient quantity and at specific areas to fill in all cracks and to add a second layer of porcelain and firing the porcelain veneer restoration on said statue to form a second bake.*

*10. The method of claim 9 in which said additional porcelain powder when applied is made to overlap the edge of said first bake.*

*11. The method of claim 9 in which the step of eroding away said statue from said porcelain veneer restoration is accomplished by blasting the former with air under pressure containing particles sufficiently hard to remove the investment material but insufficiently hard to damage the formed porcelain veneer restoration.*

* * * * *